United States Patent [19]

Colovray

[11] 3,933,929
[45] Jan. 20, 1976

[54] PROCESS FOR THE PURIFICATION OF P-NITROPHENOL

[75] Inventor: Gilbert Colovray, Peage-du-Roussillon, France

[73] Assignee: Rhone-Poulenc S.A., Paris, France

[22] Filed: May 14, 1973

[21] Appl. No.: 360,097

[30] Foreign Application Priority Data
May 15, 1972 France .............................. 72.17254

[52] U.S. Cl. .......................... 260/627 G; 260/622 R
[51] Int. Cl.² .................. C07C 37/22; C07C 37/40
[58] Field of Search ..................... 260/622 R, 627 G

[56] References Cited
UNITED STATES PATENTS

| | | | |
|---|---|---|---|
| 2,868,844 | 1/1959 | Coffield .......................... | 260/622 R |
| 3,510,527 | 5/1970 | Prosser ........................... | 260/622 R |
| 3,752,858 | 8/1973 | Odenweller ..................... | 260/622 R |

FOREIGN PATENTS OR APPLICATIONS

| | | | |
|---|---|---|---|
| 479,763 | 2/1938 | United Kingdom ............. | 260/622 R |

OTHER PUBLICATIONS
Journal Chemical Society (1921) pp. 1003–1004, London.

Berichte (1902) Band I pp. 455–456, Vol. 35.
Guttermann "Manuel Practique Chimie Organique" (1946), pp. 247–249.

Primary Examiner—James O. Thomas, Jr.
Assistant Examiner—W. B. Lone
Attorney, Agent, or Firm—Stevens, Davis, Miller & Mosher

[57] ABSTRACT

In a purification process for p-nitrophenol obtained by nitration of phenol, separation of crude nitrophenols, steam distillation to remove o-nitrophenol, and cooling the broth obtained when it contains more than 0.5% sodium bisulphite and is at pH 5.4 to 6.4 to deposit crystals of p-nitrophenol, an improvement consists in stirring the crystals with water at 55°–85°C to give a mixture containing 10–40% excess of p-nitrophenol over the solubility at that temperature, separating the upper layer of p-nitrophenol in water obtained, cooling it to 40°–50°C and separating the layer of water in p-nitrophenol, cooling the latter to below 30°C and collecting the crystals deposited.

9 Claims, No Drawings

PROCESS FOR THE PURIFICATION OF P-NITROPHENOL

This invention relates to a process for the purification of para-nitrophenol obtained by nitration of phenol.

Nitration of phenol by means of dilute or concentrated nitric acid is generally carried out in a solvent medium (e.g. an aromatic hydrocarbon) and it leads eventually to a mixture of ortho-nitrophenol and para-nitrophenol in variable proportions depending on the process used. After nitration, the residual nitric acid is decanted, the solvent is removed and, preferably after neutralisation of the organic layer containing the nitrophenols, the ortho-nitrophenol is separated by steam distillation from the para-nitrophenol. Para-nitrophenol is thus obtained in the form of a crude aqueous broth. It is then necessary to purify the nitrophenols. This purification is generally carried out by converting the nitrophenols into their sodium derivatives, isolating the latter and then converting them once again into nitrophenols [Gatterman: Practical Manual of Organic Chemistry, p. 2,478 (1946)]. It is also possible to crystallize para-nitrophenol by cooling the crude aqueous broth containing para-nitrophenol in solution when it contains more than 0.5% of sodium bisulphite and is at pH 5.4 to 6.4, and washing the crystals of para-nitrophenol with water. This latter process is described and claimed in our U.S. Pat. application Ser. No. 340,903 filed March 13, 1973 by Andre Perrin, the disclosure of which is incorporated herein by this reference.

The present invention provides a process for the preparation and purification of p-nitrophenol which comprises the steps of:

a. nitrating phenol with nitric acid;

b. separating the crude mixture of nitrophenols from the residual aqueous solution of nitric acid;

c. steam distilling ortho-nitrophenol from the crude mixture to produce a crude aqueous broth containing dissolved p-nitrophenol;

d. treating at least one of the crude aqueous broth of p-nitrophenol and the crude mixture of nitrophenols so that the crude broth or crude mixture contain more than 0.5% by weight of sodium bisulphite and is at pH 5.4 to 6.4;

e. crystallising p-nitrophenol by cooling the treated broth of step (d);

f. stirring the p-nitrophenol from step (e) in water at a temperature of 55° to 85°C, the proportions of water and p-nitrophenol being such that, at that temperature there is a 10 to 40% by weight excess of p-nitrophenol relative to the amount of p-nitrophenol which is soluble in the water at that temperature, g. separating by decantation, the liquid mixture resulting from step (f), at a temperature of 550° to 85°C, into a solution of water in p-nitrophenol which forms the lower layer, and a solution of p-nitrophenol in water, h. cooling the solution of p-nitrophenol in water, obtained in step (g) to a temperature of 40° to 50°C, separating the resulting liquid mixture by decantation into two non-miscible phases and separating the liquid phase, which is rich in p-nitrophenol, and is a solution of water in p-nitrophenol, from the liquid phase containing p-nitrophenol dissolved in water, i. cooling the liquid phase, which is rich in p-nitrophenol from step (h), to below 30°C, to cause p-nitrophenol to crystallise, and then filtering off and drying the crystals of p-nitrophenol.

During step (f) of the process, which is carried out with stirring and preferably at 65° to 75°C, the impurities are concentrated in the solution of water in p-nitrophenol. The excess of p-nitrophenol, which is preferably 20 to 30%, can be calculated easily from the solubility curve of p-nitrophenol in water, defined by N. V. SIDGWICH, Journal of Chemical Society, p. 1003 (1921). The following table gives the solubility of p-nitrophenol in water at different temperatures:

| Temperature °C | Solubility of p-nitrophenol in 100 g of water (in g) |
|---|---|
| 55 | 5.1 |
| 65 | 7.0 |
| 75 | 10.0 |
| 85 | 16.0 |

In order to adjust the ratio of p-nitrophenol to water to a value as defined in step (f), it is possible to place crude p-nitrophenol crystals in pure water, or to mix solutions of p-nitrophenol at different concentrations.

The duration of step (f) of the process is not critical. It is connected, firstly, with the efficiency of stirring, which must be sufficient to ensure intimate mixing of the two liquid phases formed, and secondly, with the way in which the mixture is heated to the desired temperature. It is possible either to pre-heat the water and/or the solutions of p-nitrophenol to the temperature chosen for step (f), or to carry out the mixing at ambient temperature and then to regulate the temperature whilst stirring. In the latter case, the duration of the temperature regulation is very largely sufficient to achieve a suitable dispersion of the phases.

Step (g) of the process consists of a decanting operation. For simplicity, this decanting is carried out at the same temperature as that reached by the mixture of water and p-nitrophenol at the end of step (f) of the process. It is possible nevertheless to alter the temperature of the mixture, after stopping the stirring and before decanting, subject to the condition of the mixture remaining within the temperature range 55°–85°C. The lower layer, consisting of a solution of water in p-nitrophenol, is collected by decanting. This solution, which is rich in impurities, is preferably then recycled to the crude aqueous broth of p-nitrophenol resulting from the steam distillation of the o-nitrophenol contained in the crude mixture of nitrophenols.

The solution of p-nitrophenol in water, resulting from the decanting and obtained during step (g) of the process, is then cooled in step (h) to a temperature of 40° to 50°C, and preferably 40° to 45°C e.g. 43°C resulting in further separation into two distinct phases. The lower layer consisting of a solution of water in p-nitrophenol is separated from the upper layer containing p-nitrophenol dissolved in water. This upper aqueous layer is then advantageously recycled in order to dissolve crude p-nitrophenol during step (f) of the process.

During step (i) of the process, the organic layer, consisting of a solution of water in p-nitrophenol, which was collected during the step (h), is cooled below 30°C in order to cause p-nitrophenol to crystallise. The final crystallisation temperature is not critical, is usually between 10° and 30°C and is generally about 20°C. p-Nitrophenol is then filtered off and dried according to the techniques of the prior art.

The process according to the invention can be carried out discontinuously or continuously. It is however particularly valuable to choose a continuous process, with recycling of the solution of p-nitrophenol in water, obtained during step (h) of the process, in order to dissolve during step (f) the p-nitrophenol to be purified. By also recycling the solution of water in p-nitrophenol, obtained during step (g) of the process to the bisulphite treatment step (d), practically quantitive purification yields of p-nitrophenol are achieved.

The crystals of p-nitrophenol obtained according to the 4-stage water extraction process, as defined above, do not contain o-nitrophenol, phenol, hydroquinone, or dinitrophenols in amounts greater than the lower limits of the detectability of these compounds by thin layer chromatography. They are only very slightly coloured and can be used directly for the production of pharmaceutical compounds of Codex quality, such as para-(acetylamino)-phenol.

In the following examples, crude p-nitrophenol is obtained in the following way: phenol dissolved in benzene is nitrated continuously by means of 58% nitric acid, and the organic layer containing the mixture of ortho- and para-nitrophenol is separated, after decanting, from the residual nitric acid. The acidic organic layer is successively neutralised by means of an aqueous solution of sodium bisulphite, distilled until the benzene has been removed and subjected to a steam distillation in order to remove the ortho-nitrophenol. An aqueous broth of crude para-nitrophenol, containing approximately 18% of p-nitrophenol, is thus obtained, 2,100 g of this aqueous broth, kept at 70°C, are removed, 40 g of a solution of sodium bisulphite containing 12 g of bisulphite are added, and 10 g of 50% sulphuric acid are introduced at this temperature so as to adjust the pH to 6. After stirring and cooling to 20°C, the crystals of crude p-nitrophenol are filtered off.

EXAMPLE 1:

A solution of p-nitrophenol in water (containing 3.85% of p-nitrophenol) is supplied continuously, at the rate of 13 kg/hour, to a flask (useful volume: 2 l), which is stirred, heated to 71°C and kept at that temperature. A solution of water in crude p-nitrophenol (containing 69.5% of p-nitrophenol) is also supplied continuously to the flask at the rate of 1.215 kg/hour. The heterogeneous mixture, which results therefrom, is passed to a decanter of useful volume 4.5 l, kept at 71°C, from which 0.319 kg/hour of the solution of water is crude p-nitrophenol (p-nitrophenol contained: 66.5%) is removed. This solution, which contains the majority of the impurities of the p-nitrophenol employed, is then purified, in the presence of sodium bisulphite at pH 6, before recycling.

At the outlet of the decanter, the solution of p-nitrophenol in water is cooled to 43° and is then introduced in the form of a heterogeneous mixture into a second decanter (capacity: 3 l) kept at 43°C. 0.870 kg/hour of a solution of water in p-nitrophenol (containing 71.3% of p-nitrophenol) is removed. The solution of p-nitrophenol in water (containing 3.85% of p-nitrophenol) which forms the upper layer is collected and is recycled in part, in order to dilute, the solution of water in crude p-nitrophenol (containing 69.5% of p-nitrophenol) used at the start of the process.

The solution of water in p-nitrophenol, containing 71.3% of p-nitrophenol), is then cooled to 20°C. The p-nitrophenol, which has precipitated, is filtered off, drained and dried. The rate of production of dry p-nitrophenol is 625 g/hour.

The purified p-nitrophenol (melting point: 115°C) is analysed by thin layer chromatography. No spots corresponding to the following compounds are detected: hydroquinone, phenol, 2,4- or 2,6-dinitro-phenol and ortho-nitrophenol. The proportions of any one of the abovementioned compounds is hence much less than 0.0250%, this being the limiting proportion corresponding to the sensitivity of the method.

EXAMPLE 2:

Following the procedure of Example 1, a solution of p-nitrophenol in water (containing 3.80% of p-nitrophenol) is supplied continuously at the rate of 13 kg/hour to the flask of useful volume 2 l, at 61°C, and a solution of water in crude p-nitrophenol (containing 69% of p-nitrophenol) is also supplied continuously at the rate of 0.6 kg/hour to the flask. The resulting heterogeneous mixture is decanted at 61°C and a solution of water in crude p-nitrophenol (containing 67% of p-nitrophenol) is removed at the rate of 0.23 kg/hour for subsequent purification by means of sodium bisulphite.

The solution of p-nitrophenol in water, resulting from the decanting, is cooled to 43°C and is then introduced in the form of a heterogeneous mixture into the second decanter. A solution of water in p-nitrophenol, containing 71.4% of p-nitrophenol, is removed at the rate of 0.353 kg/hour. The solution of p-nitrophenol in water (containing 3.8% of p-nitrophenol), which forms the upper layer, is recycled in part as in Example 1.

The solution of water in p-nitrophenol containing 71.4% of p-nitrophenol is cooled to 20°C. The p-nitrophenol which has precipitated is filtered off, drained and dried. Purified p-nitrophenol is obtained at the rate of 258 g/hour, the characteristics of which are identical to those of the product of Example 1.

EXAMPLE 3:

Following the procedure of Example 1, a solution of p-nitrophenol in water containing 3.80% of p-nitrophenol is supplied continuously at the rate of 13 kg/hour to the flask kept at 80.5°C, and a solution of water in crude p-nitrophenol (containing 69.5% of p-nitrophenol) is also supplied continuously to the flask at the rate of 2.65 kg/hour. The resulting heterogeneous mixture is decanted at 81°C and a solution of water in crude p-nitrophenol (p-nitrophenol content: 67%) is isolated by removing it at the rate of 0.880 kg/hour for subsequent purification by means of sodium bisulphite.

The solution of p-nitrophenol in water, resulting from the decanting, is cooled to 43°C and is then introduced in the form of a heterogeneous mixture into the second decanter. The solution of water in p-nitrophenol, containing 71% of p-nitrophenol, is removed at the rate of 1.820 kg/hour. The solution of p-nitrophenol in water (containing 3.8% of p-nitrophenol), which forms the upper layer, is recycled in part as in Example 1.

The solution of water in p-nitrophenol, containing 71% of p-nitrophenol, is cooled to 20°C. The p-nitrophenol, which has precipitated, is filtered off, drained and dried. Purified p-nitrophenol is obtained at the rate of 1,230 g/hour, the characteristics of which are identical to those of the product of Example 1.

We claim:

1. In a process for the purification of p-nitrophenol resulting from the nitration of phenol with nitric acid which comprises the steps of:
  i. separating the crude mixture of nitrophenols from the residual aqueous solution of nitric acid;
  ii. steam distilling ortho-nitrophenol from the crude mixture to produce a crude aqueous solution of impure p-nitrophenol;
  iii. treating at least one of the crude aqueous solution of p-nitrophenol and the crude mixture of nitrophenols with an aqueous solution of sodium bisulphite under condition such that the crude solution or crude mixture contains more than 0.5% by weight of sodium bisulphite and is at pH 5.4 to 6.4;
  iv. crystallising p-nitrophenol by cooling the treated solution of step (iii), the improvement which comprises:
  v. stirring the crystalline p-nitrophenol from step (iv) in water at a temperature of 55° to 85°C., the proportions of water and p-nitrophenol being such that, at that temperature there is a 10 to 40% by weight excess of p-nitrophenol relative to the amount of p-nitrophenol which is soluble in the water at that temperature,
  vi. separating by decantation the liquid mixture resulting from step (v) at a temperature of 55° to 85°C., into a more concentrated solution of p-nitrophenol in water, which forms the lower layer, and a less concentrated solution of p-nitrophenol in water, which forms the upper layer,
  vii. cooling the upper layer, obtained in step (vi) to a temperature of 40° to 50°C., separating the resulting liquid mixture by decantation into two non-miscible phases and separating the more concentrated solution of p-nitrophenol in water, from the less concentrated solution of p-nitrophenol in water,
  viii. cooling the more concentrated solution from step (vii), to below 30°C. to cause p-nitrophenol to crystallise, and then filtering off and drying the crystals of p-nitrophenol.

2. A process according to claim 1, wherein the less concentrated solution of p-nitrophenol in water, obtained in step (vii) is recycled to step (v) in order to dissolve the p-nitrophenol from step (iv).

3. A process according to claim 1, wherein the more concentrated solution of p-nitrophenol in water obtained in step (vi) is recycled to step (iii).

4. A process according to claim 1 wherein the temperature of step (v) is 65°–75°C.

5. A process according to claim 1 wherein the nitrophenol in step (v) is present in 20–30% excess.

6. A process according to claim 1 wherein the temperature of step (vii) is 40°–45°C.

7. A process according to claim 1 wherein the liquid phase in step (viii) is cooled to about 20°C.

8. A process according to claim 1 wherein the crude aqueous solution from step (ii) is treated in step (iii).

9. A process according to claim 1 wherein steps (v) and (vi) are carried out at a temperature of about 61°–81°C., step (vii) at about 43°C. and step (viii) at about 20°C. with recycle of the less concentrated solution of p-nitrophenol in water from step (vii) to step (v) and recycle of the more concentrated solution of p-nitrophenol in water from step (vi) to step (iii).

* * * * *